United States Patent
Kuwabara et al.

(10) Patent No.: US 9,226,724 B2
(45) Date of Patent: Jan. 5, 2016

(54) RADIOGRAPHIC IMAGING METHOD AND APPARATUS

(71) Applicant: FUJIFILM Corporation, Tokyo (JP)

(72) Inventors: Takao Kuwabara, Ashigarakami-gun (JP); Yasunori Ohta, Ashigarakami-gun (JP); Yasuko Yahiro, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 209 days.

(21) Appl. No.: 13/973,082

(22) Filed: Aug. 22, 2013

(65) Prior Publication Data

US 2013/0336444 A1 Dec. 19, 2013

Related U.S. Application Data (63) Continuation of application No. PCT/JP2012/001403, filed on Mar. 1, 2012.

(30) Foreign Application Priority Data

Mar. 4, 2011 (JP) ................. 2011-047808

(51) Int. Cl.
- *A61B 6/00* (2006.01)
- *A61B 6/02* (2006.01)
- *A61B 6/04* (2006.01)
- *A61B 6/10* (2006.01)

(52) U.S. Cl.
CPC . *A61B 6/54* (2013.01); *A61B 6/022* (2013.01); *A61B 6/0414* (2013.01); *A61B 6/10* (2013.01); *A61B 6/502* (2013.01); *A61B 6/542* (2013.01); *A61B 6/586* (2013.01)

(58) Field of Classification Search
CPC ..................................... A61B 6/0414
See application file for complete search history.

(56) References Cited

U.S. PATENT DOCUMENTS

| 5,594,772 A | 1/1997 | Toki et al. |
|---|---|---|
| 2006/0018431 A1 | 1/2006 | Kanemitsu |
| 2010/0290592 A1* | 11/2010 | Yamada ................ 378/114 |

FOREIGN PATENT DOCUMENTS

| JP | 3-251232 A | 11/1991 |
|---|---|---|
| JP | 2006-55633 A | 3/2006 |
| JP | 2010-131170 A | 6/2010 |
| JP | 2010-264194 A | 11/2010 |
| JP | 2010-279516 A | 12/2010 |

OTHER PUBLICATIONS

PCT/ISA/210—International Search Report mailed on May 1, 2012, issued in PCT/JP2012/001403.

(Continued)

*Primary Examiner* — Hoon Song
(74) *Attorney, Agent, or Firm* — Birch, Stewart, Kolasch & Birch, LLP (57) ABSTRACT

In a case where a series of operations of an imaging sequence are continuously performed when an imaging switch is continuously in ON state, if the imaging switch is turned into OFF state only for a given period and the given period is not more than a predetermined threshold value, control is exerted such that part of the operations of the imaging sequence is continuously performed.

10 Claims, 6 Drawing Sheets

(56) References Cited

OTHER PUBLICATIONS

PCT/ISA/237—mailed on May 1, 2012, issued in PCT/JP2012/001403.

Chinese Office Action and Search Report dated Mar. 23, 2015, for Chinese Application No. 201280011759.9 with the English translation.

* cited by examiner

| OPERATOR | THRESHOLD VALUE OF OFF PERIOD |
|---|---|
| A | $T_A$ |
| B | $T_B$ |
| C | $T_C$ |
| ⋮ | ⋮ |

RADIOGRAPHIC IMAGING METHOD AND APPARATUS

CROSS REFERENCE TO RELATED APPLICATIONS

This application is the Continuation of PCT/JP2012/001403 filed on Mar. 1, 2012, which claims priority under 35 U.S.C. 119(a) to Patent Application No. 2011-047808 filed in Japan on Mar. 4, 2011, all of which are hereby expressly incorporated by reference into the present application.

TECHNICAL FIELD

The present invention relates to a radiographic imaging method and a radiographic imaging apparatus, wherein radiation is applied to the subject from each of different imaging directions to detect a radiographic image for each imaging direction.

BACKGROUND ART

It is conventionally known that stereoscopic viewing utilizing parallax can be achieved by combining and displaying a plurality of images. Such an image that allows stereoscopic viewing (which will hereinafter be referred to as "stereoscopic image" or "stereo image") is generated based on a plurality of images that are obtained by imaging the same subject from different directions and therefore have a parallax therebetween.

Generation of a stereoscopic image in this manner is used not only in the fields of digital cameras and televisions but also in the field of radiographic imaging. Namely, radiation is applied to the subject from different directions, and each radiation transmitted through the subject is detected with a radiographic image detector to obtain a plurality of radiographic images having a parallax therebetween, and a stereoscopic image is generated based on these radiographic images (see, for example, Japanese Unexamined Patent Publication No. 2010-279516). By generating a stereoscopic image in this manner, a radiographic image that provides feel of depth can be observed, which is more suitable for diagnosis.

On the other hand, a tomosynthesis imaging apparatus, wherein a radiation source is moved to apply radiation to the subject from different imaging directions, similarly to a radiographic imaging apparatus for taking the above-described stereoscopic image, has been proposed (see, for example, Japanese Unexamined Patent Publication No. 2010-131170). This tomosynthesis imaging apparatus performs imaging operations with applying radiation to the subject from different imaging directions, as described above, and adds up a plurality of radiographic images obtained by the imaging operations to provide an image where a desired slice plane is emphasized.

DISCLOSURE OF INVENTION

Radiographic imaging apparatuses, in general, are configured such that a series of operations of an imaging sequence including application of radiation are performed while the imaging switch of the apparatus is pressed by the operator, and the imaging sequence is stopped when the operator has released the imaging switch, in view of safety.

However, for example, in a case where the operator has accidentally released the imaging switch for a brief instant of time or the imaging switch is turned into OFF state for a brief instant of time due to chattering or electrical noise, it may be inconvenient to stop the entire imaging sequence.

Specifically, in a case where mammographic imaging, for example, is performed using the above-described apparatus for taking a stereoscopic image or the tomosynthesis imaging apparatus, a plurality of imaging operations are performed in a state where the breast is compressed with a compression paddle. In this case, if the compression by the compression paddle is released when the imaging sequence is stopped, as described above, then, when the imaging switch is pressed again to restart the imaging sequence and the breast is compressed again, it is almost impossible to provide the shape of the breast that is the same as the shape before the imaging sequence is stopped. Therefore, different shapes of the breast are imaged by the plurality of imaging operations and it is impossible to obtain an appropriate stereoscopic image or tomographic image.

Further, if a shut-down operation of the X-ray tube is performed when the imaging switch is turned into OFF state and the imaging sequence is stopped during the plurality of imaging operations, it takes a long time for completing a start-up operation of the X-ray tube when the imaging switch is pressed again and the imaging sequence is restarted, resulting in a longer imaging time. In particular, in the case of mammographic imaging, the imaging operations are performed in the state where the breast is compressed, as described above, and a longer imaging time means a greater burden on the patient.

In view of the above-described circumstances, the present invention is directed to providing a radiographic imaging method and a radiographic imaging apparatus which allows immediate return to a normal imaging sequence when the operator has accidentally released the imaging switch for a brief instant of time or the imaging switch is turned into OFF state for a brief instant of time due to chattering or electrical noise, as described above, thereby allowing taking appropriate radiographic images.

The radiographic imaging apparatus of the invention is a radiographic imaging apparatus including: a radiation exposure unit for applying radiation emitted from a radiation source to a subject from different imaging directions; a radiographic image detector for detecting a radiographic image for each imaging direction generated by the application of radiation by the radiation exposure unit; and an imaging control unit for exerting control such that a series of operations of an imaging sequence including the application of radiation from each imaging direction are continuously performed when an imaging switch is continuously in ON state, wherein if the imaging switch is turned into OFF state only for a given period and the given period is not more than a predetermined threshold value, the imaging control unit continuously performs part of the operations of the imaging sequence.

In the above-described radiographic imaging apparatus of the invention, the subject may be a breast and the apparatus may include a compression paddle for compressing the breast, and wherein, if the period of the OFF state is not more than the threshold value, the imaging control unit may continue compression by the compression paddle as the part of the operations of the imaging sequence, or if the period of the OFF state is longer than the threshold value, the imaging control unit may release the compression by the compression paddle.

The radiation source may include an X-ray tube, and if the period of the OFF state is not more than the threshold value, the imaging control unit may continue a start-up operation of the X-ray tube as the part of the operations of the imaging sequence, or if the period of the OFF state is longer than the threshold value, the imaging control unit may exert control to perform a shut-down operation of the X-ray tube.

If a period of the OFF state of the imaging switch is not more than the threshold value, the imaging control unit may stop the application of radiation.

If a period of the OFF state of the imaging switch is not more than the threshold value, the imaging control unit may stop movement of the radiation source.

The threshold value may be not smaller than one second and not greater than two seconds.

The radiographic imaging apparatus may include a threshold value setting reception unit for receiving an arbitrary value set as the threshold value.

A plurality of values may be set in advance for the threshold value.

A plurality of values for different operators may be set in advance for the threshold value.

The imaging control unit may receive information of the operator and sets the threshold value corresponding to the received information of the operator.

The radiographic imaging method of the invention is a radiographic imaging method including: applying radiation emitted from a radiation source to a subject from different imaging directions; detecting a radiographic image for each imaging direction generated by the application of radiation; and continuously performing a series of operations of an imaging sequence including the application of radiation from each imaging direction when an imaging switch is continuously in ON state, wherein, if the imaging switch is turned into OFF state only for a given period and the given period is not more than a predetermined threshold value, part of the operations of the imaging sequence is continuously performed.

According to the radiographic imaging method and the radiographic imaging apparatus of the invention, if the imaging switch is turned into OFF state only for a given period and the given period is not more than a predetermined threshold value, part of the operations of the imaging sequence is continued. Therefore, for example, the compression by the compression paddle and the start-up operation of the X-ray tube, as described above, can be continuously performed without being stopped, and the operation can immediately be returned to the normal imaging sequence, thereby allowing taking an appropriate stereoscopic image or tomographic image.

Further, with the above-described radiographic imaging apparatus of the invention, in the case where the application of radiation is stopped even if the period of the OFF state of the imaging switch is not more than the threshold value, the application of radiation can immediately be stopped when the imaging switch is turned into OFF state by the operator not accidentally but to stop the imaging sequence, thereby ensuring safety with respect to exposure to the radiation.

Further, in the case where the movement of the radiation source is stopped even if the period of the OFF state of the imaging switch is not more than the threshold value, the movement of the radiation source can immediately be stopped when the imaging switch is turned into OFF state by the operator not accidentally but to stop the imaging sequence, thereby avoiding the situation where the radiation source hits the subject, for example.

Still further, in the case where a plurality of values for different operators are set in advance for the threshold value of the period of the OFF state of the imaging switch, the threshold value can be set according to a request from each operator, thereby providing higher convenience for each operator.

DESCRIPTION OF PREFERRED EMBODIMENTS

Figure 1:
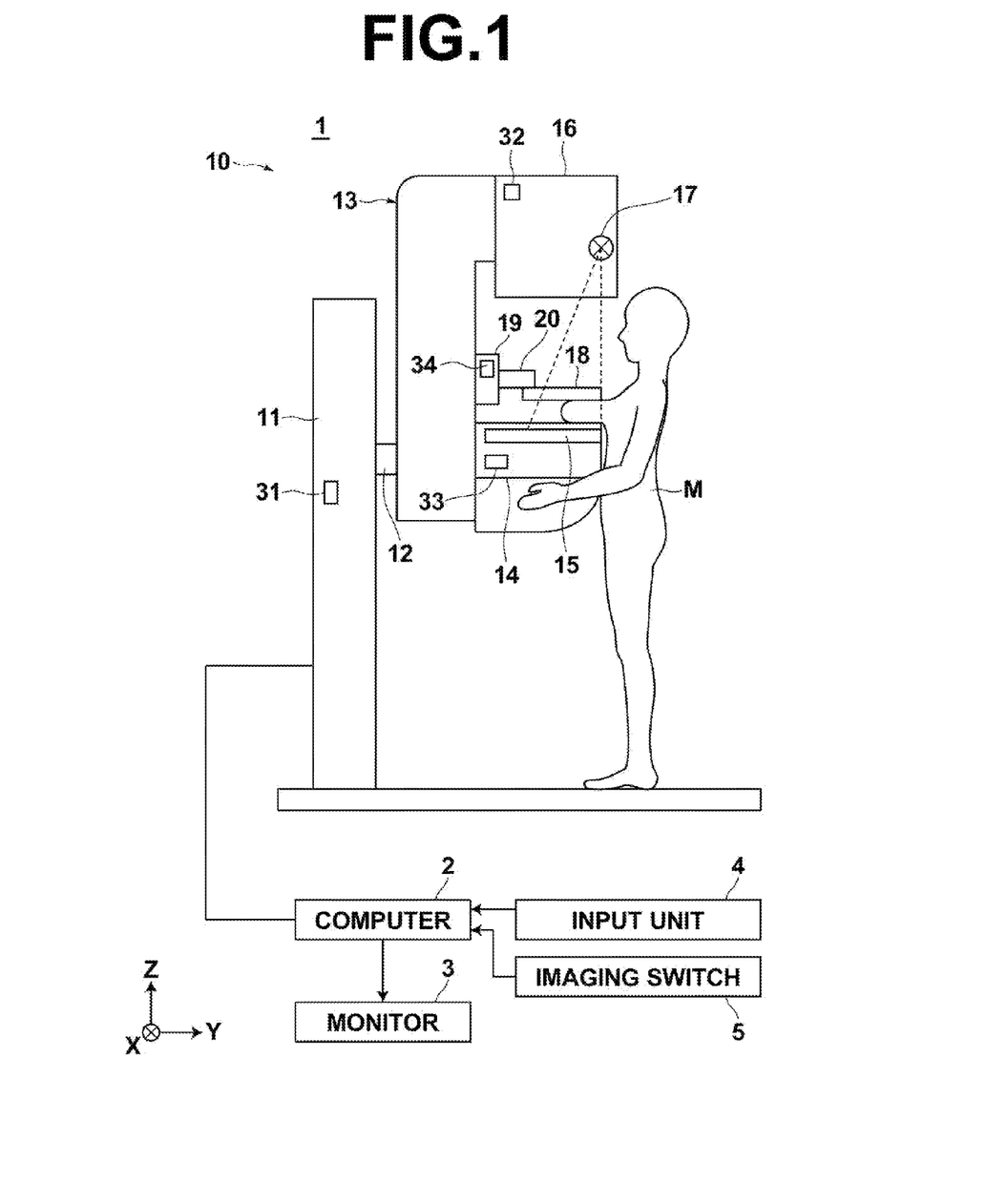
FIG. 1 is a diagram illustrating the schematic configuration of a mammographic imaging and display system which employs one embodiment of a radiographic imaging apparatus of the invention.

Hereinafter, a mammographic imaging and display system employing one embodiment of a radiographic imaging apparatus of the invention will be described with reference to the drawings. FIG. 1 is a diagram illustrating the schematic configuration of the entire mammographic imaging and display system of this embodiment.

As shown in FIG. 1, the mammographic imaging and display system 1 of this embodiment includes a mammographic imaging apparatus 10, a computer 2 connected to the mammographic imaging apparatus 10, and a monitor 3, an input unit 4 and an imaging switch 5 connected to the computer 2.

Figure 2:
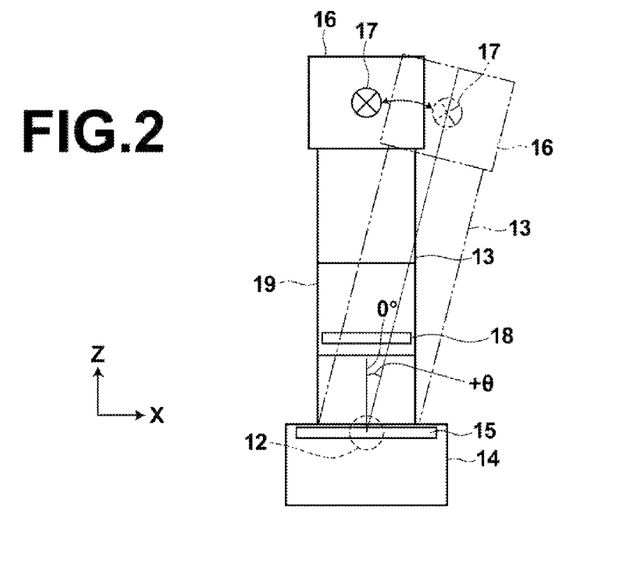
FIG. 2 is a diagram illustrating a state where a radiation source unit in the mammographic imaging and display system shown in FIG. 1 is moved.

As shown in FIG. 1, the mammographic imaging apparatus 10 includes a base 11, a rotation shaft 12 that is rotatable and is movable in the vertical direction (Z-direction) relative to the base 11, and an arm 13 that is connected to the base 11 via the rotation shaft 12. FIG. 2 shows the arm 13 viewed from the right side of FIG. 1.

The arm 13 is C-shaped, and provided with an imaging table 14, where a breast is placed, at one end thereof and a radiation source unit 16 at the other end thereof such that the radiation source unit 16 faces the imaging table 14. The movement of the arm 13 in the vertical direction is controlled by an arm controller 31, which is built in the base 11.

The imaging table 14 contains therein a radiographic image detector 15, such as a flat panel detector, and a detector controller 33, which controls reading of electric charge signals from the radiographic image detector 15, etc.

The imaging table 14 also contains therein a circuit board, etc. The circuit board includes a charge amplifier for converting electric charge signals read out from the radiographic image detector 15 into voltage signals, a correlated double sampling circuit for sampling the voltage signals outputted from the charge amplifier, an AD converter for converting the voltage signals into digital signals, etc.

The radiographic image detector 15 is of a type that is repeatedly usable to record and read a radiographic image. The radiation detector 15 may be a so-called direct-type radiographic image detector, which directly receives the radiation and generates electric charges, or may be a so-called indirect-type radiographic image detector, which once converts the radiation into visible light, and then converts the visible light into electric charge signals. As the reading system to read out the radiographic image signal, a so-called TFT reading system that reads out the radiographic image signal with turning on and off TFT (thin film transistor) switches, or a so-called optical reading system that reads out the radiographic image signal by applying reading light may be used; however, this is not intended to limit the invention, and any other system may be used.

The radiation source unit 16 contains therein a radiation source 17 and a radiation source controller 32. The radiation source 17 includes an X-ray tube. The X-ray tube includes a capacitor, which is used when a high tube voltage is applied, and an anode, which emits radiation when being hit by electron beams while being rotated. The radiation source controller 32 controls a start-up operation and a shut-down operation of the X-ray tube of the radiation source 17, timing of application of radiation from the radiation source 17, radiation generation conditions (such as tube current, time, tube voltage, etc.) at the radiation source 17, etc.

Further, at the middle portion of the arm 13, a compression paddle 18 disposed above the imaging table 14 for holding and compressing the breast, a support 20 for supporting the compression paddle 18, and a moving mechanism 19 for moving the support 20 in the vertical direction are disposed. The position and the compressing pressure of the compression paddle 18 are controlled by a compression paddle controller 34.

Figure 3:
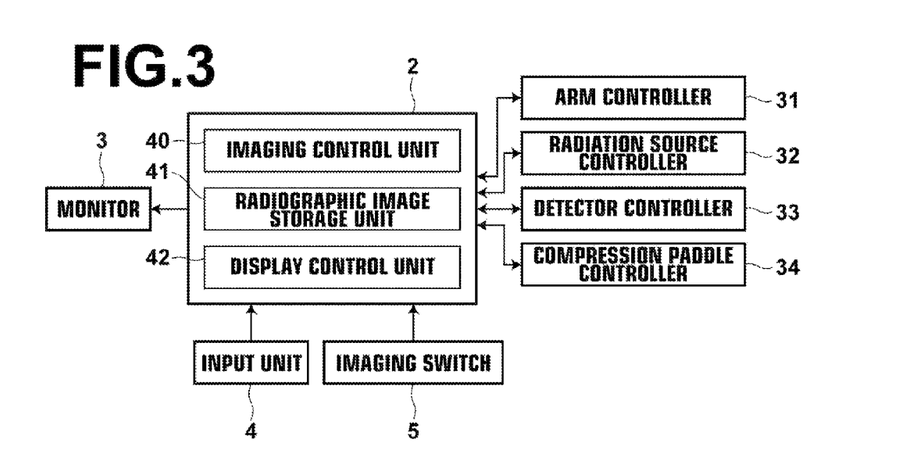
FIG. 3 is a block diagram illustrating the schematic internal configuration of a computer of the mammographic imaging and display system shown in FIG. 1.

The computer 2 includes a central processing unit (CPU), a storage device, such as a semiconductor memory, a hard disk, a SSD, etc., and these hardware devices form an imaging control unit 40, a radiographic image storage unit 41 and a display control unit 42, as shown in FIG. 3.

The imaging control unit 40 outputs predetermined control signals to the controllers 31 to 34 to control the imaging sequence of the entire system. A specific control method will be described in detail later.

The radiographic image storage unit 41 stores two radiographic image signals detected by the radiographic image detector 15 in imaging operations from two different imaging directions.

The display control unit 42 applies predetermined signal processing to the radiographic image signals read out from the radiographic image storage unit 41 and then displays a stereo image of the breast on the monitor 3.

The input unit 4 is formed by a pointing device, such as a keyboard and a mouse, and receives an input by the operator, such as an input of imaging conditions.

The imaging switch 5 is a button used to instruct to perform a series of operations of an imaging sequence including the imaging operations from two different imaging directions. While the imaging switch 5 is pressed by the operator and is in ON state, the imaging control unit 40 of the computer 2 controls the individual units so that the series of operations of the imaging sequence are performed. In a case where the imaging switch 5 is turned into OFF state due to the operator accidentally releasing the imaging switch 5 or due to chattering or electrical noise, for example, the imaging control unit 40 stops or continues part of the operations in the imaging sequence depending on the length of period of the OFF state. How the part of operations in the imaging sequence is controlled will be described in detail later.

The monitor 3 is configured to be capable of displaying a stereo image using two radiographic image signals outputted from the computer 2. As an example of an arrangement for displaying a stereo image, an arrangement where two radiographic images based on two radiographic image signals are displayed using two screens, and one of the radiographic images is directed to the right eye of the observer and the other of the radiographic images is directed to the left eye of the observer by using a half mirror or a polarizing glass to achieve display of a stereo image may be employed. Alternatively, for example, an arrangement where two radiographic images are displayed with being superimposed one another and offset from one another by a distance corresponding to a predetermined parallax and the displayed image is observed through polarizing glasses to achieve generation of a stereo image, or an arrangement where two radiographic images are displayed on a 3D liquid crystal display that allows stereoscopic viewing, such as a display of the parallax barrier system or the lenticular system, to achieve generation of a stereo image may be employed.

Figure 4:
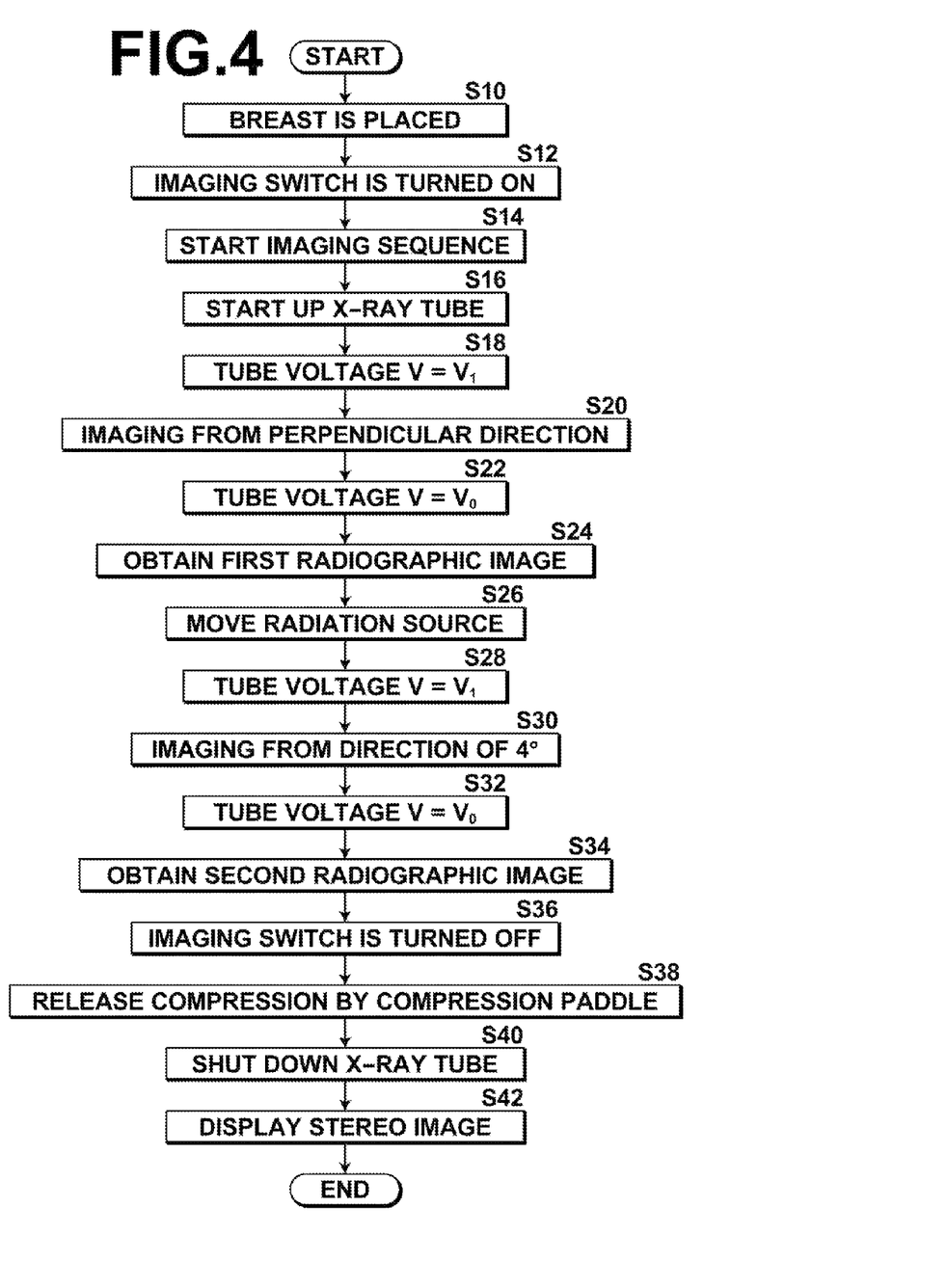
FIG. 4 is a flow chart for explaining operation of the mammographic imaging and display system employing one embodiment of the radiographic imaging apparatus of the invention.
Figure 5:
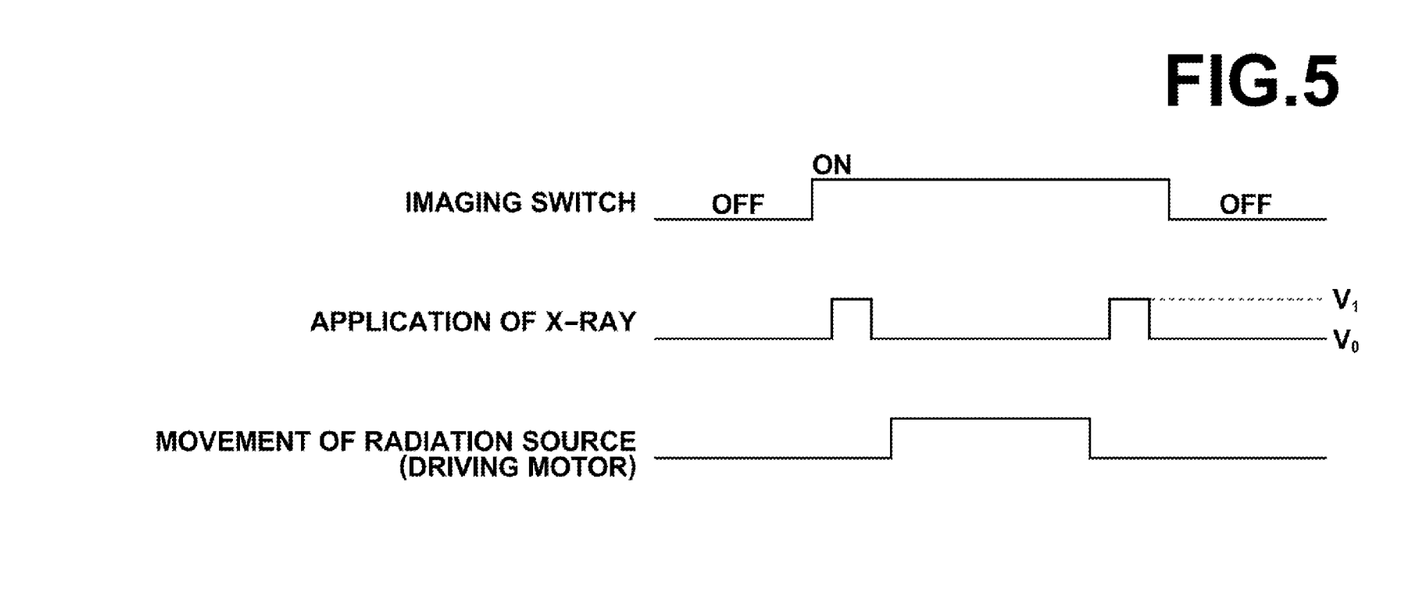
FIG. 5 is a timing chart showing ON/OFF state of an imaging switch, timing of application of radiation from a radiation source and timing of moving the radiation source during a series of operations of an imaging sequence.

Next, operation of the mammographic imaging and display system of this embodiment is described with reference to the flow chart shown in FIG. 4 and the timing chart shown in FIG. 5. FIG. 5 shows ON/OFF state of the imaging switch 5, timing of application of radiation from the radiation source 17, and timing of moving the radiation source 17 (operation timing of a driving motor for moving the radiation source 17) during a series of operations of an imaging sequence. First, a series of operations of the imaging sequence in a case where the imaging switch 5 is not turned into the above-described OFF state during the imaging sequence are described.

First, after power supplies to the mammographic imaging apparatus 10, the computer 2 and the monitor 3 are turned on, the breast of a subject M is placed on the imaging table 14 and the breast is compressed by the compression paddle 18 with a predetermined pressure (S10).

Then, when the operator presses the imaging switch 5, the imaging switch 5 is turned into ON state, as shown in FIG. 5 (S12), and the imaging sequence is started by the imaging control unit 40 (S14). Specifically, first, a control signal is outputted from the imaging control unit 40 to the radiation source controller 32. In response to the inputted control signal, the radiation source controller 32 starts the start-up operation of the X-ray tube of the radiation source 17 (S16). The start-up operation of the X-ray tube may include, for example, starting rotation of the anode, charging the capacitor, etc.

After the start-up operation of the X-ray tube of the radiation source 17 is finished, the imaging control unit 40 performs an imaging operation to take a first radiographic image among two radiographic images forming a stereo image.

Specifically, first, the imaging control unit 40 reads out imaging angles θ set in advance for taking a stereo image, and outputs information of the read-out imaging angles θ to the arm controller 31. In this embodiment, it is assumed that θ=0° and θ=4° are stored in advance as the information of the imaging angles θ; however, this is not intended to limit the invention, and any imaging angles can be set by operator via the input unit 4.

The arm controller 31 receives the information of the imaging angles, θ=0° and θ=4°, outputted from the imaging control unit 40. Then, in response to the control signal outputted from the imaging control unit 40, the arm controller 31 outputs, first, a control signal for moving the arm 13 to be perpendicular to the imaging table 14, as shown in FIG. 2, based on the information of θ=0°.

In the state where the arm 13 has been moved to be perpendicular to the imaging table 14 in response to the control signal outputted from the arm controller 31, the imaging control unit 40 outputs a control signal to the radiation source controller 32 and the detector controller 33 to apply radiation and read out a radiographic image signal.

In response to the inputted control signal, the radiation source controller 32 starts application of the tube voltage ($V=V_1$) at the radiation source 17, thereby starting the first application of radiation shown in FIG. 5 (S18).

Then, a radiographic image of the breast taken from the direction of 0° by the first application of radiation from the radiation source 17 is detected by the radiographic image detector 15 (S20).

When a radiation application period of one shot, which is set in advance as shown in FIG. 5, has elapsed, the radiation source controller 32 sets the tube voltage at the radiation source 17 to be $V=V_0$, thereby ending the first application of radiation (S22). It should be noted that $V_0$ is a tube voltage at which emission of the radiation from the radiation source 17 is stopped, and may be a certain voltage around 5V or may be 0V.

Then, the detector controller 33 reads out a radiographic image signal from the radiographic image detector 15 and applies predetermined signal processing to the radiographic image signal. The radiographic image signal subjected to the signal processing is stored in the radiographic image storage unit 41 of the computer 2 (S24).

After the first radiographic image has been taken, as described above, operation to move the radiation source unit 17, as shown in FIG. 5, is started (S26).

Specifically, in response to the control signal outputted from the imaging control unit 40, the arm controller 31 outputs a control signal for rotating the arm 13 by an angle of +θ° relative to the direction perpendicular to the imaging table 14, as shown in FIG. 2. Namely, in this embodiment, a control signal for rotating the arm 13 by an angle of 4° relative to the direction perpendicular to the imaging table 14 is outputted.

Based on the control signal outputted from the arm controller 31, the arm 13 is moved in the direction of 4°, and the radiation source unit 16 is also moved in the direction of 4°.

In the state where the arm 13 has been rotated by 4° in response to the control signal outputted from the arm controller 31, the imaging control unit 40 outputs a control signal to the radiation source controller 32 and the detector controller 33 to apply radiation and read out a radiographic image signal.

In response to the inputted control signal, the radiation source controller 32 starts application of the tube voltage ($V=V_1$) at the radiation source 17, thereby starting the second application of radiation shown in FIG. 5 (S28).

Then, a radiographic image of the breast taken from the direction of 4° by the second application of radiation from the radiation source 17 is detected by the radiographic image detector 15 (S30).

When the radiation application period of one shot, which is set in advance as shown in FIG. 5, has elapsed, the radiation source controller 32 sets the tube voltage at the radiation source 17 to be $V=V_0$, thereby ending the second application of radiation (S32).

Then, the detector controller 33 reads out a radiographic image signal from the radiographic image detector 15 and applies predetermined signal processing to the radiographic image signal. The radiographic image signal subjected to the signal processing is stored in the radiographic image storage unit 41 of the computer 2 (S34).

When the imaging operations to take the two radiographic images forming a stereo image, as described above, are finished, the operator releases the imaging switch 5, thereby turning the imaging switch 5 into OFF state. When the imaging operations have been finished and the imaging switch 5 has been turned into OFF state, the imaging control unit 40 ends the imaging sequence and outputs a control signal to the compression paddle controller 34. In response to the inputted control signal, the compression paddle controller 34 releases the compression of the breast by the compression paddle 18 (S38).

Further, the imaging control unit 40 outputs a control signal to the radiation source controller 32. In response to the inputted control signal, the radiation source controller 32 performs the shut-down operation of the X-ray tube of the radiation source 17 of the radiation source unit 16 (S40). The shut-down operation of the X-ray tube herein may include, for example, stopping the rotation of the anode, stopping the charging of the capacitor, etc.

Then, the two radiographic image signals stored in the radiographic image storage unit 41, as described above, are read out by the display control unit 42. The display control unit 42 applies predetermined processing to these radiographic image signals, and the processed radiographic image signals are outputted to the monitor 3. Then, a radiographic image for the right eye and a radiographic image for the left eye are displayed on the monitor 3, thereby achieving display of the stereo image of the breast (S42).

The series of operations in a normal imaging sequence have been described. Next, operations in a case where the imaging switch 5 is accidentally turned into OFF state during a period from a point of time at which the imaging switch 5 is pressed by the operator to a point of time at which the operator releases the imaging switch 5 after two radiographic images are taken is described with reference to the flow chart shown in FIG. 6.

Figure 6:
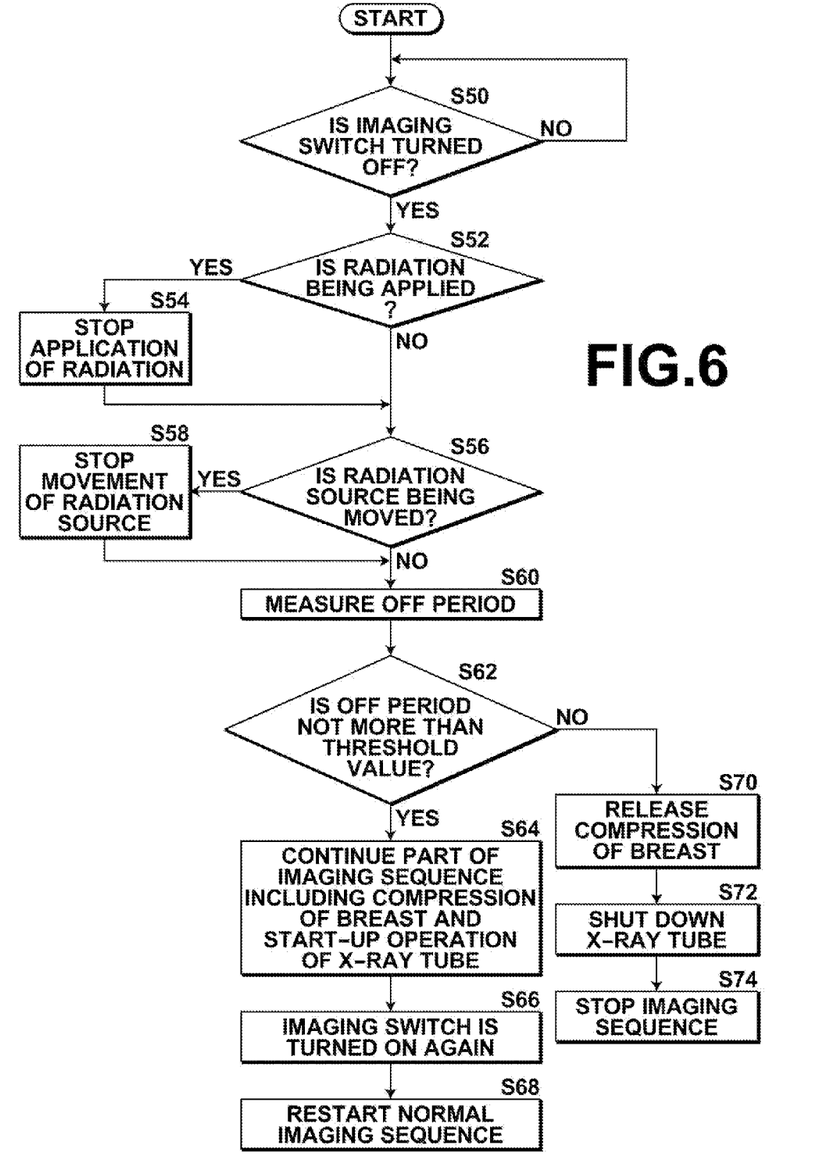
FIG. 6 is a flow chart for explaining operation of the mammographic imaging and display system employing one embodiment of the radiographic imaging apparatus of the invention when the imaging switch is accidentally turned into OFF state.

When the imaging switch 5 is accidentally turned into OFF state after a point of time at which the imaging switch 5 is pressed by the operator (S50: YES) due to the operator accidentally releasing the imaging switch 5 or due to chattering or electrical noise, for example, then, if radiation is being applied from the radiation source 17 at that time, that is, if it is during the first application of radiation (where the tube voltage $V=V_1$) or the second application of radiation (where the tube voltage $V=V_1$) shown in FIG. 5 (S52: YES), the imaging control unit 40 outputs a control signal to the radiation source controller 32, and the radiation source controller 32 stops the application of radiation (S54). Further, at this time, if the radiation source 17 is being moved (S56: YES), the imaging control unit 40 outputs a control signal to the arm controller 31, and the arm controller 31 stops the movement of the arm 13 (the radiation source unit 16) (S58).

The imaging control unit 40 measures a time elapsed from the point of time at which the imaging switch 5 is turned into OFF state (S60). If the period of the OFF state (OFF period) is not more than a predetermined threshold value (S62: YES), operations in the imaging sequence other than the application of radiation and the movement of the radiation source 17 described above are continuously performed (S64). Specifically, for example, the compression of the breast by the compression paddle 18, the start-up state of the X-ray tube of the radiation source 17, etc., are maintained.

Then, when the imaging switch 5 is turned into ON state while the OFF period is still not more than the predetermined threshold value because the imaging switch 5 is pressed by the operator again or the influence of chattering or electrical noise has disappeared (S66), the imaging control unit 40 restarts the movement of the radiation source 17 and continuously performs the normal imaging sequence (S68).

In contrast, if the OFF period of the imaging switch 5 has exceeded the predetermined threshold value (S62: NO), the imaging control unit 40 outputs a control signal to the compression paddle controller 34. In response to the inputted control signal, the compression paddle controller 34 releases the compression of the breast by the compression paddle 18 (S70). Further, the imaging control unit 40 outputs a control signal to the radiation source controller 32. In response to the inputted control signal, the radiation source controller 32 performs the shut-down operation of the X-ray tube of the radiation source 17 (S72). Then, the imaging control unit 40 stops the imaging sequence (S74).

According to the mammographic imaging and display system of the above-described embodiment, when the imaging switch it turned into OFF state only for a given period, if the OFF period is not more than a predetermined threshold value, the compression by the compression paddle, the start-up operation of the X-ray tube, etc., are continuously performed without being stopped. Therefore, the operation can immediately be returned to the normal imaging sequence, thereby allowing taking an appropriate stereo image.

Although only the compression of the breast and the start-up operation of the X-ray tube, among the series of operations of the imaging sequence, are continuously performed when the OFF period of the imaging switch 5 is not more than a predetermined threshold value in the above-described embodiment, this is not intended to limit the invention, and any other operation may also be continued.

That is, the reason of continuing the compression of the breast is that, once the compression of the breast is released, the shape of the breast changes when the breast is compressed again and it is impossible to take an appropriate stereo image. Therefore, any other operation that is undesirable to be stopped in view of taking an appropriate stereo image may also be continued.

Further, the reason of not stopping the start-up operation of the X-ray tube is that, once the X-ray tube is shut down, it takes time to start up the X-ray tube again. Therefore, any other operation that is undesirable to be stopped in view of the time taken for returning to the normal operation may also be continued.

Still further, although the movement of the radiation source unit 16 is stopped when the imaging switch 5 is turned into OFF state in the above-described embodiment, this operation is set in view of safety and is not intended to limit the invention. In a case where higher priority is set on reduction of the imaging time than on safety, for example, the movement of the radiation source unit 16 may be continued when the imaging switch 5 is turned into OFF state and the OFF period is not more than a predetermined threshold value.

It is desirable that the threshold value of the OFF period used in the above-described embodiment is set to be not smaller than one second and not greater than two seconds, for example.

Further, the threshold value of the OFF period may be set in advance or may arbitrarily be set by the operator via the input unit 4. Still further, a plurality of threshold values may be set in advance for the OFF period, and the operator may select one of the threshold values via the input unit 4 so that the selected threshold value is set.

Figure 7:
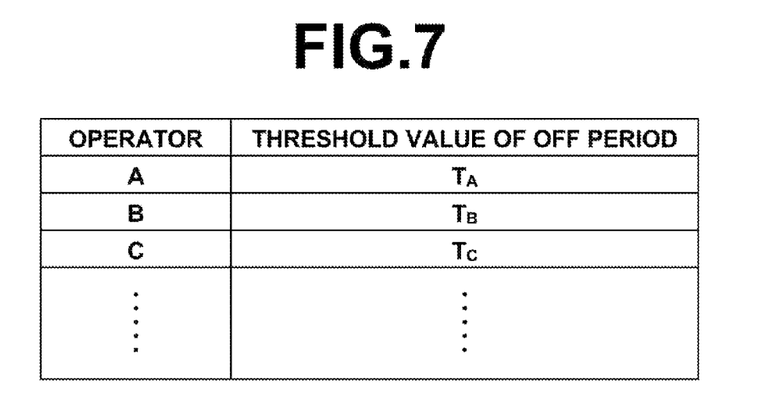
FIG. 7 is a diagram illustrating one example of a table that associates each of a plurality of operators with a threshold value of OFF period that is set in advance for the operator.

Yet further, as shown in FIG. 7, threshold values ($T_A$, $T_B$, $T_C$, . . . ) of the OFF period for different operators (A, B, C, . . . ) may be set in advance as a table, and information of operator may be received via the input unit 4 so that the threshold value of the OFF period correspond to the received information of operator is set.

Further, although the radiographic imaging apparatus of the invention is applied to an imaging apparatus that takes a stereo image of the breast in the above-described embodiment, this is not intended to limit the invention. The radiographic imaging apparatus of the invention is applicable to any other apparatus that takes a plurality of radiographic image from different imaging directions by moving the radiation source, such as a tomosynthesis imaging apparatus.

What is claimed is:

1. A radiographic imaging apparatus comprising:
a radiation exposure unit for applying radiation emitted from a radiation source to a subject from different imaging directions;
a radiographic image detector for detecting a radiographic image for each imaging direction generated by the application of radiation by the radiation exposure unit; and
an imaging control unit for exerting control such that a series of operations of an imaging sequence including the application of radiation from each imaging direction are continuously performed when an imaging switch is continuously in ON state,
wherein if the imaging switch is turned into OFF state only for a given period and the given period is not more than a predetermined threshold value, the imaging control unit continuously performs part of the operations of the imaging sequence, wherein
the subject is a breast and the apparatus comprises a compression paddle for compressing the breast, and
if the period of the OFF state is not more than the threshold value, the imaging control unit continues compression by the compression paddle as the part of the operations of the imaging sequence, or if the period of the OFF state is longer than the threshold value, the imaging control unit releases the compression by the compression paddle.

2. The radiographic imaging apparatus as claimed in claim 1, wherein the radiation source comprises an X-ray tube, and
wherein, if the period of the OFF state is not more than the threshold value, the imaging control unit continues a start-up operation of the X-ray tube as the part of the operations of the imaging sequence, or if the period of the OFF state is longer than the threshold value, the imaging control unit exerts control to perform a shut-down operation of the X-ray tube.

3. The radiographic imaging apparatus as claimed in claim 1, wherein, if the period of the OFF state of the imaging switch is not more than the threshold value, the imaging control unit stops the application of radiation.

4. The radiographic imaging apparatus as claimed in claim 1, wherein, if the period of the OFF state of the imaging switch is not more than the threshold value, the imaging control unit stops movement of the radiation source.

5. The radiographic imaging apparatus as claimed in claim 1, wherein the threshold value is not smaller than one second and not greater than two seconds.

6. The radiographic imaging apparatus as claimed in claim 1, comprising a threshold value setting reception unit for receiving an arbitrary value set as the threshold value.

7. The radiographic imaging apparatus as claimed in claim 1, wherein a plurality of values are set in advance for the threshold value.

8. The radiographic imaging apparatus as claimed in claim 7, wherein a plurality of values for different operators are set in advance for the threshold value.

9. The radiographic imaging apparatus as claimed in claim 8, wherein the imaging control unit receives information of the operator and sets the threshold value corresponding to the received information of the operator.

10. A radiographic imaging method comprising:
applying radiation emitted from a radiation source to a subject from different imaging directions;
detecting a radiographic image for each imaging direction generated by the application of radiation; and
continuously performing a series of operations of an imaging sequence including the application of radiation from each imaging direction when an imaging switch is continuously in ON state, wherein, if the imaging switch is turned into OFF state only for a given period and the given period is not more than a predetermined threshold value, part of the operations of the imaging sequence is continuously performed, wherein
the subject is a breast, and
if the period of the OFF state is not more than the threshold value, compression of the breast is continued, by a compression paddle, as the part of the operations of the imaging sequence, or if the period of the OFF state is longer than the threshold value, the compression of the breast is released by the compression paddle.

* * * * *